(12) United States Patent
Bosua et al.

(10) Patent No.: US 12,318,203 B2
(45) Date of Patent: *Jun. 3, 2025

(54) VEHICLE INTERFACE SYSTEMS AND METHODS FOR ANALYTE-BASED ACCESS CONTROL

(71) Applicant: Know Labs, Inc., Seattle, WA (US)

(72) Inventors: Phillip Bosua, Seattle, WA (US);
Ronald Erickson, Seattle, WA (US);
Peter Conley, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 176 days.

This patent is subject to a terminal disclaimer.

(21) Appl. No.: 17/887,954

(22) Filed: Aug. 15, 2022

(65) Prior Publication Data

US 2024/0050007 A1 Feb. 15, 2024

(51) Int. Cl.
*B60R 25/25* (2013.01)
*A61B 5/00* (2006.01)
(Continued)

(52) U.S. Cl.
CPC ........... *A61B 5/18* (2013.01); *A61B 5/117* (2013.01); *A61B 5/14546* (2013.01);
(Continued)

(58) Field of Classification Search
CPC ..... A61B 5/18; A61B 5/14546; A61B 5/6893; A61B 5/4845; A61B 5/117;
(Continued)

(56) References Cited

U.S. PATENT DOCUMENTS

| 4,202,000 A | 5/1980 | Carballes |
|---|---|---|
| 6,005,520 A | 12/1999 | Nalbandian et al. |

(Continued)

FOREIGN PATENT DOCUMENTS

| EP | 3146898 B1 | 11/2018 |
|---|---|---|
| EP | 3981329 A1 | 4/2022 |

(Continued)

OTHER PUBLICATIONS

Saadat et al., Physical Layer Biometrics Using Antennas for Secure Wearable Wireless Communication, 2018, IEEE, p. 2677-2686 (Year: 2018).*

(Continued)

*Primary Examiner* — McDieunel Marc
(74) *Attorney, Agent, or Firm* — HSML P.C.

(57) ABSTRACT

Access to a vehicle is controlled based on the presence or amount of one or more analytes in a potential driver. The one or more analytes are detected using a non-invasive analyte sensor. The non-invasive analyte sensor may be included in a steering wheel of the vehicle, a touch point in the vehicle, or a mobile device of the potential driver. The one or more analytes are indicative of an identity and/or a status of the potential driver. The status of the potential driver may include the presence of amounts above a threshold for one or more intoxicants and/or indicators of tiredness or sickness. The access is based on the identity and/or status of the potential driver as indicated by the presence or amount of the one or more analytes.

23 Claims, 5 Drawing Sheets

(51) Int. Cl.
  *A61B 5/117* (2016.01)
  *A61B 5/145* (2006.01)
  *A61B 5/18* (2006.01)
  *B60R 25/02* (2013.01)
  *B60R 25/04* (2013.01)
  *B60R 25/102* (2013.01)

(52) U.S. Cl.
  CPC .......... *A61B 5/4845* (2013.01); *A61B 5/6893* (2013.01); *B60R 25/02* (2013.01); *B60R 25/04* (2013.01); *B60R 25/102* (2013.01); *B60R 25/25* (2013.01); *B60R 2325/10* (2013.01)

(58) Field of Classification Search
  CPC . A61B 5/14532; A61B 5/0507; B60R 25/102; B60R 25/02; B60R 25/04; B60R 25/25; B60R 2325/10
  See application file for complete search history.

(56) References Cited

U.S. PATENT DOCUMENTS

| | | | |
|---|---|---|---|
| 7,295,827 B2 | 11/2007 | Liu et al. | |
| 8,223,021 B2 | 7/2012 | Goodnow et al. | |
| 8,734,535 B2 * | 5/2014 | Blum | B01D 9/0063 23/296 |
| 8,882,670 B2 | 11/2014 | Hancock | |
| 9,198,607 B2 | 12/2015 | Fischer | |
| 9,367,067 B2 * | 6/2016 | Gilmore | G05D 1/12 |
| 9,864,024 B2 | 1/2018 | Vester | |
| 10,149,629 B2 | 12/2018 | Szczepaniak et al. | |
| 10,258,268 B2 | 4/2019 | Roblyer et al. | |
| 10,405,785 B2 | 9/2019 | Ho et al. | |
| 10,478,101 B1 | 11/2019 | Cespedes et al. | |
| 10,548,503 B2 | 2/2020 | Bosua | |
| 10,617,296 B2 | 4/2020 | Sloan et al. | |
| 10,856,766 B2 | 12/2020 | Leabman | |
| 10,912,500 B2 | 2/2021 | Poeze et al. | |
| 10,932,698 B2 | 3/2021 | Leath et al. | |
| 10,956,950 B2 | 3/2021 | Al-Ali et al. | |
| 11,031,970 B1 | 6/2021 | Bosua | |
| 11,033,208 B1 | 6/2021 | Bosua | |
| 11,058,317 B1 | 7/2021 | Bosua | |
| 11,058,331 B1 | 7/2021 | Bosua | |
| 11,063,373 B1 | 7/2021 | Bosua | |
| 11,193,923 B2 | 12/2021 | Bosua | |
| 11,202,582 B2 | 12/2021 | Verkruijsse et al. | |
| 11,223,383 B2 | 1/2022 | Bosua | |
| 11,234,618 B1 | 2/2022 | Bosua et al. | |
| 11,234,619 B2 | 2/2022 | Bosua | |
| 11,244,753 B2 | 2/2022 | Haggerty et al. | |
| 11,284,819 B1 | 3/2022 | Bosua et al. | |
| 11,284,820 B1 | 3/2022 | Bosua et al. | |
| 11,291,374 B2 | 4/2022 | Lee et al. | |
| 11,298,037 B2 | 4/2022 | Leabman | |
| 11,330,997 B2 | 5/2022 | Bosua | |
| 11,350,830 B2 | 6/2022 | McKenna et al. | |
| 11,360,188 B2 | 6/2022 | Leabman | |
| 11,367,525 B2 | 6/2022 | Addison et al. | |
| 11,389,093 B2 | 7/2022 | Triman et al. | |
| 11,426,104 B2 | 8/2022 | Schurman et al. | |
| 11,511,156 B2 * | 11/2022 | Shavit | A61B 5/1123 |
| 11,747,463 B2 * | 9/2023 | Nagpal | H04L 67/12 342/59 |
| 2001/0005183 A1 | 6/2001 | Nevermann et al. | |
| 2003/0036713 A1 | 2/2003 | Bouton et al. | |
| 2004/0065158 A1 | 4/2004 | Schrepfer et al. | |
| 2004/0127777 A1 | 7/2004 | Ruchti et al. | |
| 2004/0133086 A1 | 7/2004 | Ciurczak et al. | |
| 2004/0235536 A1 | 11/2004 | Kim et al. | |
| 2009/0213025 A1 | 8/2009 | Coupez et al. | |
| 2009/0275814 A1 | 11/2009 | Watanabe et al. | |
| 2010/0041969 A1 | 2/2010 | Beise | |
| 2011/0028814 A1 | 2/2011 | Petersen et al. | |
| 2011/0217423 A1 * | 9/2011 | Vaman | A23G 4/20 426/282 |
| 2013/0096396 A1 | 4/2013 | Riedel | |
| 2014/0101772 A1 * | 4/2014 | Anzai | G06F 21/83 726/26 |
| 2014/0213870 A1 | 7/2014 | Hsu et al. | |
| 2016/0051171 A1 | 2/2016 | Pikov et al. | |
| 2016/0361002 A1 | 12/2016 | Palikaras et al. | |
| 2017/0095667 A1 | 4/2017 | Yakovlev et al. | |
| 2017/0181658 A1 | 6/2017 | Dettmann et al. | |
| 2018/0028824 A1 | 2/2018 | Pivonka et al. | |
| 2018/0132766 A1 | 5/2018 | Lee et al. | |
| 2019/0008422 A1 | 1/2019 | Leath et al. | |
| 2019/0053741 A1 | 2/2019 | Chaudhry | |
| 2019/0104939 A1 | 4/2019 | Costantine et al. | |
| 2019/0179008 A1 | 6/2019 | Tavassolian et al. | |
| 2019/0269853 A1 | 9/2019 | Doyle et al. | |
| 2019/0353752 A1 | 11/2019 | Lin et al. | |
| 2019/0357800 A1 | 11/2019 | Bosua | |
| 2019/0374135 A1 | 12/2019 | Poeze et al. | |
| 2019/0388000 A1 | 12/2019 | Costantine et al. | |
| 2020/0054255 A1 | 2/2020 | Conrad et al. | |
| 2020/0057163 A1 | 2/2020 | Bromberg | |
| 2020/0146584 A1 | 5/2020 | Bosua | |
| 2020/0187791 A1 | 6/2020 | Leabman | |
| 2020/0187792 A1 | 6/2020 | Leabman | |
| 2020/0187793 A1 | 6/2020 | Leabman | |
| 2020/0187812 A1 | 6/2020 | Leabman | |
| 2020/0187813 A1 | 6/2020 | Leabman | |
| 2020/0187814 A1 | 6/2020 | Leabman | |
| 2020/0187815 A1 | 6/2020 | Leabman | |
| 2020/0187816 A1 | 6/2020 | Leabman | |
| 2020/0187817 A1 | 6/2020 | Leabman | |
| 2020/0187818 A1 | 6/2020 | Leabman | |
| 2020/0187819 A1 | 6/2020 | Leabman | |
| 2020/0187820 A1 | 6/2020 | Leabman | |
| 2020/0187836 A1 | 6/2020 | Leabman | |
| 2020/0187837 A1 | 6/2020 | Leabman | |
| 2020/0187867 A1 | 6/2020 | Leabman | |
| 2020/0191909 A1 | 6/2020 | Leabman | |
| 2020/0191932 A1 | 6/2020 | Leabman | |
| 2020/0191933 A1 | 6/2020 | Leabman | |
| 2020/0191944 A1 | 6/2020 | Leabman | |
| 2020/0191945 A1 | 6/2020 | Leabman | |
| 2020/0191947 A1 | 6/2020 | Leabman | |
| 2020/0192426 A1 | 6/2020 | Leabman | |
| 2020/0192427 A1 | 6/2020 | Leabman | |
| 2020/0192428 A1 | 6/2020 | Leabman | |
| 2020/0193326 A1 | 6/2020 | Leabman | |
| 2020/0195197 A1 | 6/2020 | Leabman | |
| 2020/0195293 A1 | 6/2020 | Leabman | |
| 2020/0375549 A1 | 12/2020 | Wexler et al. | |
| 2021/0059587 A1 | 3/2021 | Feldman et al. | |
| 2021/0076988 A1 | 3/2021 | Wang et al. | |
| 2021/0186357 A1 | 6/2021 | Bosua et al. | |
| 2021/0259571 A1 | 8/2021 | Bosua | |
| 2021/0259592 A1 | 8/2021 | Bosua | |
| 2021/0259593 A1 | 8/2021 | Bosua | |
| 2022/0015695 A1 | 1/2022 | Margarito et al. | |
| 2022/0031254 A1 | 2/2022 | Al-Ali et al. | |
| 2022/0192494 A1 | 6/2022 | Leabman | |
| 2022/0192531 A1 | 6/2022 | Leabman | |
| 2022/0248984 A1 | 8/2022 | Poeze et al. | |
| 2024/0039838 A1 * | 2/2024 | Garcarz | H04L 41/22 |

FOREIGN PATENT DOCUMENTS

| | | |
|---|---|---|
| JP | 2012125382 A | 7/2012 |
| JP | 2014147637 A | 8/2014 |
| KR | 1020160081740 A | 7/2016 |
| WO | 2017163245 A1 | 9/2017 |
| WO | 2019071138 A1 | 4/2019 |
| WO | 2019182638 A1 | 9/2019 |
| WO | 2019198567 A1 | 10/2019 |
| WO | 2019217461 A1 | 11/2019 |
| WO | 2020006077 A1 | 1/2020 |
| WO | 2020037171 A1 | 2/2020 |

(56) References Cited

FOREIGN PATENT DOCUMENTS

| WO | 2021198045 A1 | 10/2021 |
|---|---|---|
| WO | 2022026623 A1 | 2/2022 |

OTHER PUBLICATIONS

Oluwole et al., Modeling of RF security system using smart antennas, 2015, IEEE, p. 118-122 (Year: 2015).*

Will et al., Human Target Detection, Tracking, and Classification Using 24-GHz FMCW Radar, 2019, IEEE, p. 7283-7299 (Year: 2019).*

Bianchi et al., Unveiling Access Point Signal Instability in WiFi-Based Passive Sensing, 2017, IEEE, pg. (Year: 2017).*

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, mailed Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

International Search Report and Written Opinion issued for International Patent Application No. PCT/IB2020/062222, Date of mailing: Mar. 25, 2021, 7 pages.

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

International Search Report and Written Opinion issued for International Patent Application No. PCT/IB2021/050805, Date of mailing: May 4, 2021, 8 pages.

International Search Report and Written Opinion issued for International Patent Application No. PCT/IB2021/050838, Date of mailing: May 6, 2021, 7 pages.

Mankowska, A. et al., "Association of C-Reactive Protein and Other Markers of Inflammation with Risk of Complications in Diabetic Subjects," The Journal Of The International Federation Of Clinical Chemistry And Laboratory Medicine, Mar. 2006, 17(1), pp. 8-11.

Mahendran, Y. et al., "Association of Ketone Body Levels With Hyperglycemia and Type 2 Diabetes in 9,398 Finnish Men," Diabetes, Oct. 2013, 62(10), pp. 3618-3626.

Nall, R., "Alcoholic Liver Cirrhosis," Healthline, Updated on Sep. 17, 2018, URL: https://www.healthline.com/health/alcoholic-liver-cirrhosis (Retrieved on May 3, 2021), 4 pages.

Allin, K. et al., "Elevated C-reactive protein in the diagnosis, prognosis, and cause of cancer," Abstract, Crit Rev Clin Lab Sci., Jul.-Aug. 2011, 48(4), 1 page (Retrieved from URL: https://pubmed.ncbi.nlm.nih.gov/22035340/ on May 5, 2021).

"Luteinizing Hormone (LH) Levels Test," MedlinePlus, URL: https://medlineplus.gov/lab-tests/luteinizing-hormone-lh-levels-test/ (Retrieved on May 5, 2021), 6 pages.

Kim, J. et al., "Noninvasive Alcohol Monitoring Using a Wearable Tattoo-Based Iontophoretic-Biosensing System," ACS Sens. Jan. 2016, pp. 1011-1019.

Bravo-Arrabal, J. et al., "Development and Implementation of a Hybrid Wireless Sensor Network of Low Power and Long Range for Urban Environments," Sensors 2021, 21, 567, 27 pages.

Guo, X. et al., "Noninvasive in-vehicle alcohol detection with wavelength-modulated differential photothermal radiometry," Biomedical Optics Express, 2014, vol. 5, No. 7, pp. 2333-2340.

International Search Report and Written Opinion issued for International Patent Application No. PCT/IB2023/058072, Date of mailing: Nov. 13, 2023, 9 pages.

* cited by examiner

VEHICLE INTERFACE SYSTEMS AND METHODS FOR ANALYTE-BASED ACCESS CONTROL

FIELD

This disclosure is directed to controls for access to vehicles based on non-invasive detection of one or more analytes and determinations of identity or status of individuals seeking access based on the one or more analytes.

BACKGROUND

Intoxicated driving and tired driving are major causes of severe accidents. Further, limiting vehicle access to specific users, through keys, other identification devices, and the like, is a useful security feature for preventing unauthorized use or theft of vehicles. Detection of intoxication prior to vehicle use is primarily done using ignition interlock devices that use breath-based alcohol measurements before allowing a vehicle to be started.

SUMMARY

This disclosure is directed to controls for access to vehicles based on non-invasive detection of one or more analytes and determinations of identity or status of individuals seeking access based on the one or more analytes.

By using non-invasive analyte detection to control use of a vehicle, the ability to use a vehicle can be conditioned on an identity and status of the potential driver. The status can be an intoxication status determined based on the presence and/or amount of analytes, which can be indicative of not only alcohol intoxication, but other intoxicants as well, providing more comprehensive prevention of intoxicated driving. Further, the combination of determining identity while also checking the status of the potential driver reduces the likelihood of circumvention of such controls. Additionally, the one or more analytes can include biomarkers indicative of other potential states of the driver such as tiredness, sickness, and the like, and optionally, vehicle access can also be conditioned on these other states of the driver.

In an embodiment, a vehicle access control system includes a sensor. The sensor includes an antenna array having at least one transmit antenna and at least one receive antenna. The at least one transmit antenna is positioned and arranged to transmit a transmit signal into a human target, and the at least one receive antenna is positioned and arranged to detect a response resulting from transmission of the transmit signal by the at least one transmit antenna into the human target. The sensor further includes a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum and a receive circuit that is electrically connectable to the at least one receive antenna, the receive circuit is configured to receive a response detected by the at least one receive antenna. The vehicle access control system further includes a controller configured to determine an identity and/or status of the human target, based on a presence and/or amount of one or more analytes determined by processing of the response, and determine an access permission for a vehicle based at least in part on the identity and/or status of the individual.

In an embodiment, the sensor is included in the vehicle. In an embodiment, the sensor is included in a mobile device and the mobile device includes an antenna configured to send a communication signal to the vehicle. In an embodiment, the controller is included in the mobile device. In an embodiment, the controller is included in the vehicle. In an embodiment, the controller is disposed at a remote server. In an embodiment, the access permission is based on the identity of the human target. In an embodiment, the access permission is based on the status of the human target. In an embodiment, the status is based on an amount of the one or more analytes in the human target. In an embodiment, the one or more analytes include one or more intoxicants. In an embodiment, the access permission is based on both the identity and the status of the human target.

In an embodiment, a vehicle includes an access mechanism, an access control sensor, and a controller. The access control sensor includes an antenna array having at least one transmit antenna and at least one receive antenna. The at least one transmit antenna is positioned and arranged to transmit a transmit signal into a human target, and the at least one receive antenna is positioned and arranged to detect a response resulting from transmission of the transmit signal by the at least one transmit antenna into the human target. The access control sensor further includes a transmit circuit that is electrically connectable to the at least one transmit antenna. The transmit circuit is configured to generate a transmit signal to be transmitted by the at least one transmit antenna, the transmit signal is in a radio or microwave frequency range of the electromagnetic spectrum. The access control sensor also includes a receive circuit that is electrically connectable to the at least one receive antenna, the receive circuit is configured to receive a response detected by the at least one receive antenna. The controller is configured to determine an identity and/or status of the human target, based on a presence and/or amount of one or more analytes determined by processing of the response, and control the access mechanism based on the determined identity and/or status of the human target.

In an embodiment, wherein the access control is an ignition of the vehicle. In an embodiment, the access control is a controller configured to control an electric motor of the vehicle. In an embodiment, the access control is a door lock of the vehicle. In an embodiment, the sensor is disposed in a control of the vehicle. In an embodiment, the control of the vehicle is a steering wheel of the vehicle. In an embodiment, the sensor is disposed in a panel provided in a driver section of the vehicle.

In an embodiment, a method of controlling use of a vehicle including non-invasively detecting one or more analytes. Non-invasively detecting the one or more analytes includes generating a transmit signal using a transmit circuit of a sensor, transmitting the transmit signal into a human target using a transmit antenna of the sensor, the transmit signal in a radio or microwave frequency range of the electromagnetic spectrum, detecting a response resulting from transmitting the transmit signal into the human target using a receive antenna of the sensor, and processing the response to determine a presence or amount of the one or more analytes in the human target. The method of controlling use of the vehicle further includes determining, based on the presence or amount of the one or more analytes in the human target, an identity and/or status of the human target and operating an access mechanism of the vehicle based on the identity and/or status of the human target.

In an embodiment, operating the access mechanism of the vehicle includes preventing access to or operation of the vehicle when the status of the individual includes intoxication.

In an embodiment, a method of controlling use of a motor vehicle includes confirming a biological identity of an individual using a non-invasive sensor by transmitting, using at least one transmit antenna, first transmit signals in a radio or microwave frequency range of the electromagnetic spectrum into the individual and detecting responses resulting from transmitting the first transmit signals into the individual using at least one receive antenna. The method further includes determining a presence and/or amount of an analyte in the individual using a non-invasive sensor by transmitting, using at least one transmit antenna, second transmit signals in a radio or microwave frequency range of the electromagnetic spectrum into the individual and detecting responses resulting from transmitting the second transmit signals into the individual using at least one receive antenna. The method further includes permitting or blocking access to or operation of the motor vehicle based on the confirming and the determining.

In an embodiment, the non-invasive sensor used in the confirming is the same non-invasive sensor used in the determining. In an embodiment, the non-invasive sensor used in the confirming is different from the non-invasive sensor used in the determining.

DETAILED DESCRIPTION

This disclosure is directed to controls for access to vehicles based on non-invasive detection of one or more analytes and determinations of identity or status of individuals seeking access based on the one or more analytes.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. Examples of detecting an analyte using a non-invasive spectroscopy sensor operating in the radio or microwave frequency range of the electromagnetic spectrum are described in WO 2019/217461, U.S. Pat. Nos. 11,063,373, 11,058,331, 11,033,208, 11,284,819, 11,284,820, 10,548,503, 11,234,619, 11,031,970, 11,223,383, 11,058,317, 11,193,923, and 11,234,618, the entire contents of which are incorporated herein by reference.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, one or more microbes, combinations thereof, and the like.

The analyte(s) can be any analyte that one may wish to detect. The analyte can be human or non-human, animal or non-animal, biological or non-biological. For example, the analyte(s) can include, but is not limited to, one or more of glucose, alcohol, white blood cells, or luteinizing hormone. The analyte(s) can include, but is not limited to, a chemical, a combination of chemicals, a virus, bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, one or more microbes, or combinations thereof. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; ketones, alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase;

glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* polio virus, *Pseudomonas aeruginosa,* respiratory syncytial virus, rickettsia (scrub typhus), *Schistosoma mansoni, Toxoplasma gondii, Trepenoma pallidium, Trypanosoma cruzi*/rangeli, vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition or metabolites thereof, with non-limiting examples including ethanol or other alcohols; ketones; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

In an embodiment, the one or more analyte(s) can be detected in some or all of a plurality of tissues, bodily fluids, and the like that are subjected to a transmit signal, in turn resulting in a response signal. For example, a transmit signal into a subject at a location where the transmit signal passes through, for example, skin, bone, muscle, interstitial fluid, blood vessels, and blood can result in a response signal indicative of the presence and/or amount of analytes present in some or all of the tissues and/or fluids that the transmit signal enters into or passes through. In embodiments, the response signal can be indicative of the presence and/or amount of some or all of a plurality of organs, such as the liver, the pancreas, the kidneys, the gallbladder, and/or any other such organ. In an embodiment, the response signal can be parsed based on characteristics thereof to estimate or determine the presence and/or amount of the analyte(s) in particular tissues and/or bodily fluids, for example the presence and/or amount of the analyte specifically present in blood, interstitial fluid, a particular tissue or organ, or the like.

Figure 1:
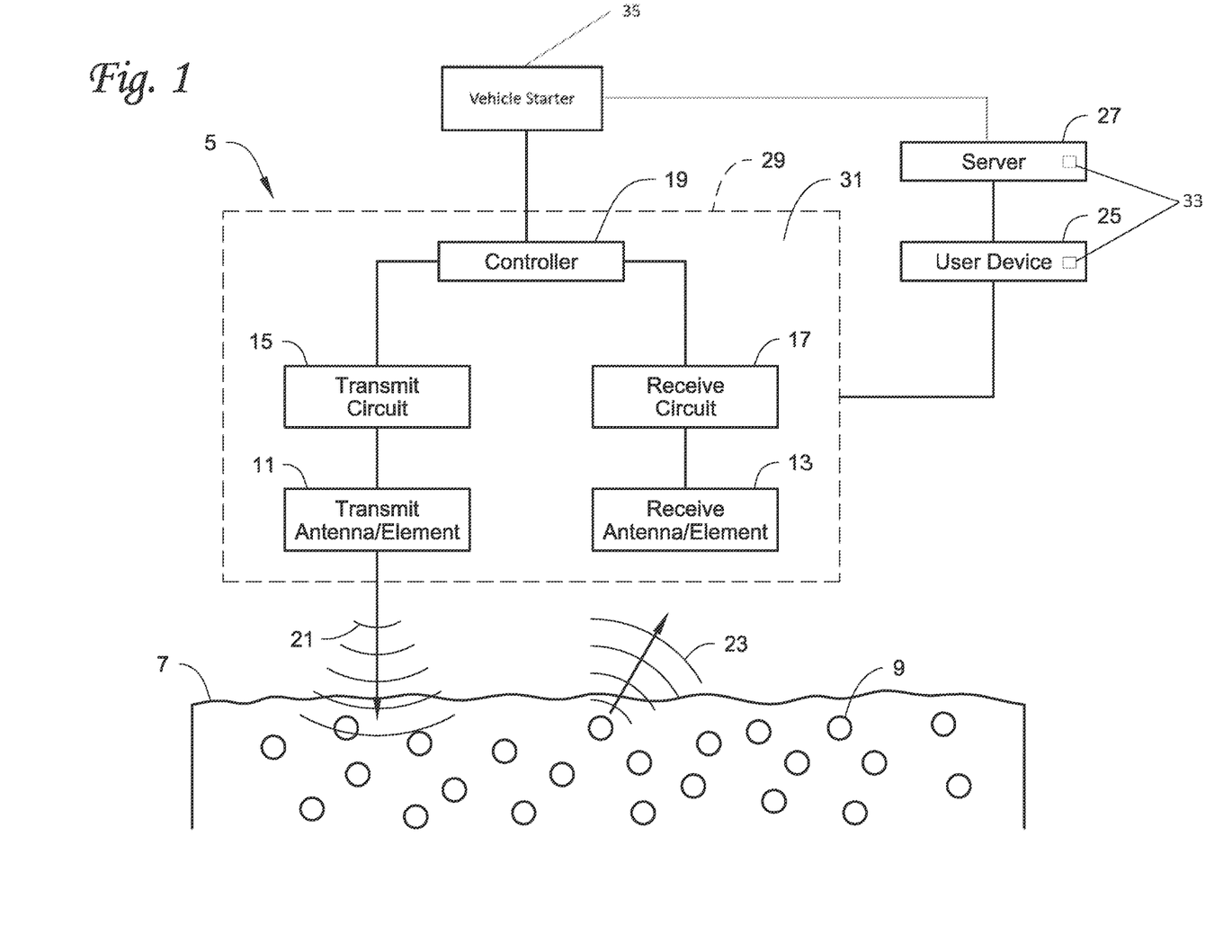
FIG. 1 shows a sensor system according to an embodiment.

FIG. 1 shows a sensor at a measurement location according to an embodiment. An embodiment of a non-invasive analyte sensor system with a non-invasive analyte sensor 5 is illustrated. The sensor 5 is depicted relative to a target 7 that contains one or more analyte(s) of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). Sensor 5 can be a non-invasive sensor. Non-invasive sensing can include sensing without disruption to tissue of a subject, for example without requiring injection, implantation into the subject, or the like. It is understood that while sensor 5 is a non-invasive sensor capable of non-invasive sensing, it can also be used to detect the one or more analytes in samples that have been obtained from a subject such as blood or tissue samples.

The analyte(s) of interest 9 are to be detected at target 7. The target can be one or more parts of a person seeking access to the vehicle based on detection of the one or more analytes by the sensor 5. For example, the target 7 can be any one or more of, for example, the lower left leg, upper left leg, lower right leg, upper right leg, lower left arm, upper left arm, groin, abdomen, chest, neck, and/or the head of the individual seeking access to the vehicle such as a potential driver.

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 includes a frequency in the range from about 10 kHz to about 100 GHz. In another embodiment, the frequency can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz.

The receive antenna 13 is positioned, arranged, and configured to detect one or more electromagnetic response signals 23 that result from the transmission of the transmit signal 21 by the transmit antenna 11 into the target 7 and impinging on the analyte(s) 9. The receive antenna 13 can be an electrode or any other suitable receiver of electromagnetic signals in the radio frequency (RF) or microwave range. In an embodiment, the receive antenna 13 is configured to detect electromagnetic signals including a frequency in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7. When the target 7 is a living subject or a part thereof, the signal obtained by receive antenna 13 can be indicative of the analyte(s) present in at least both the blood and the interstitial fluid of the living subject.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27. In an embodiment, the controller 19 is further configured to determine an action to be taken in response to detection of the analyte or analytes of interest 9. In an embodiment, another controller (not shown) separate from controller 19 can determine the action.

In an embodiment, controller 19 can be configured to determine a presence and/or amount of the one or more analytes at the uncalibrated sensing location based on the return signal. In an embodiment, the external device 25 or remote server 27 can include a controller 33 configured to determine the presence and/or amount of the one or more analytes at the uncalibrated sensing location based on the return signal. At least one of controllers 19 or 33 is configured to determine an identity and/or a status of the individual including the target 7 based on the presence and/or amount of the one or more analytes. The determination of identity and/or status can be based by comparing the presence and/or amount of the one or more analytes to values for the one or more analytes that are associate with or indicative of the identity and/or the status of the individual. Identity can be a specific identity of an individual, confirmation that the individual is part of a particular group, or the like. Status can be a current state of the individual such as an intoxication status based on the presence and/or amount of one or more intoxicants such as alcohol, prescription or recreational drugs, or the like. Other example statuses can include tiredness or exhaustion, attentiveness, sickness, and the like. These statuses can be based on the presence and/or amounts of least some of the one or more analytes such as biomarkers associated with the statuses, drugs or associated compounds having the statuses as a side effect or resulting condition, particular pathogens or indicators thereof, and the like. Based on the particular identity and/or status, at least one of the controllers 19 and/or 33 can determine an access permission for the individual including target 7. The access permission is determined based on the identity and/or status of the individual. The access permission can be based at least in part on the identity of the individual, such as being an owner, lessee, or renter of the vehicle, being an agent or employee of an owner, lessee, or renter, or the like. The access permission can be based at least in part on the status of the individual, such as not being intoxicated by alcohol and/or other drugs, in a state of sufficient alertness, or the like. In embodiments, both the identity and the status can be used to determine the access permission, such as only allowing access to specific persons to operate the vehicle, and controlling such access conditionally based on the status of that individual. In embodiments, additional external factors can be included in the determination of the access permission, such as date, time, and the like. For example, operation of a vehicle can be restricted to certain dates and/or ranges of hours in addition to the identity and/or the status of the individual seeking access. The controller 19 and/or 33 can communicate with a vehicle starter 35 to provide or prevent operation of the vehicle based on the determined access control. In an embodiment, the vehicle starter can be an engine ignition, a controller of an engine such as a controller of a combustion engine or an electric engine, a shifter used to place a vehicle into gear, or the like.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29. In an embodiment, the housing 29 can be included in a mobile device, such as a wearable device or mobile phone of a potential driver of a vehicle. In an embodiment, the housing 29 can be provided on or in a vehicle, for example in a steering wheel such as the steering wheel 60 shown in FIG. 3 and described below, a door handle of the vehicle, or in an access interface such as access interface 76 shown in FIG. 4 and described below. In an embodiment, the housing 29 can be at least part of an access control device such as a key, key fob, or the like.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain (S21) and an increased reflection at output (S22) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte(s) 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

Further information on the sensor 5 and its components and variations thereof can be found in U.S. Pat. Nos. 11,063,373, 11,234,619, 11,031,970, 11,223,383, 11,058,317, 11,058,331, 11,193,923, 10,548,503, 11,330,997, 11,033,208, 11,234,618, 11,284,819, and 11,284,820, the entire contents of which are incorporated herein by reference in their entirety.

Figure 2:
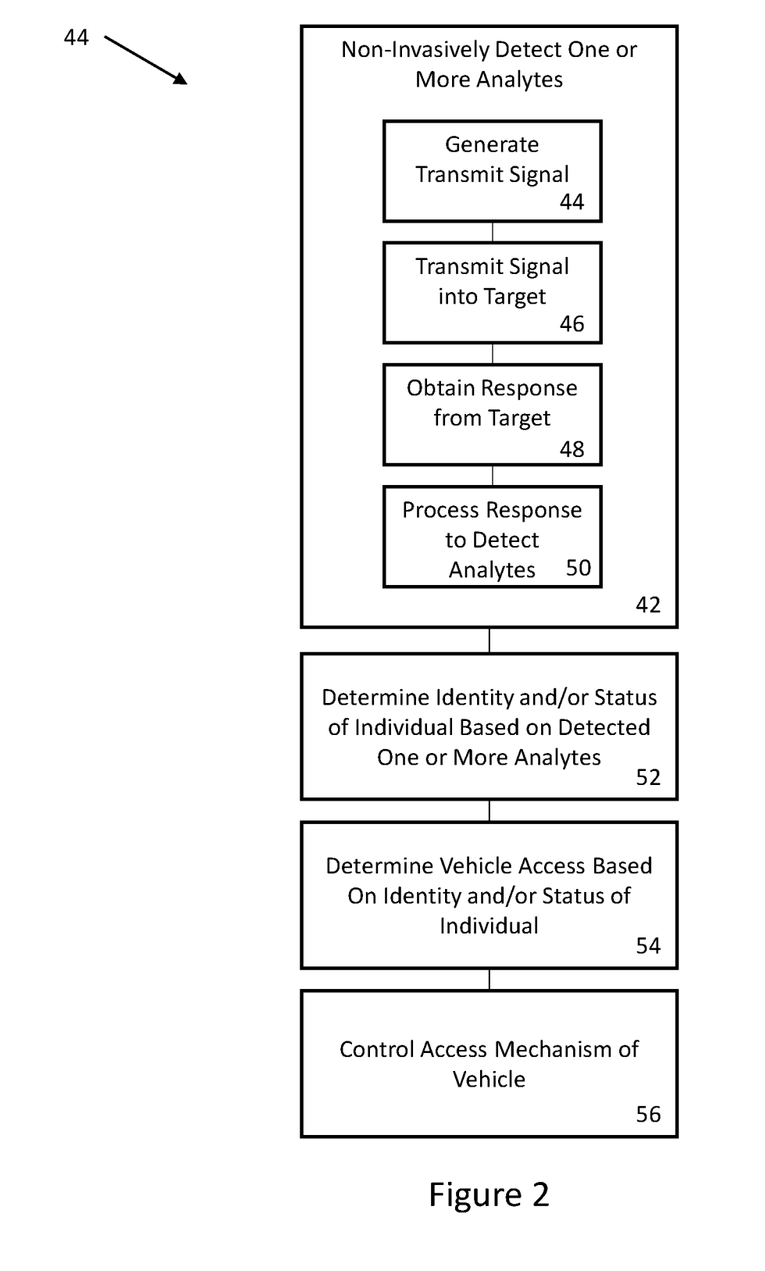
FIG. 2 shows a flowchart of a method controlling access to a vehicle according to an embodiment.

FIG. 2 shows a flowchart of a method controlling access to a vehicle according to an embodiment. Method 40 includes non-invasively detecting one or more analytes 42. The non-invasive detection at 42 includes generating a transmit signal 44, transmitting the transmit signal into a target 46, receiving a response at 48, and processing the response 50. The method 40 further includes determining an identity and/or a status of the individual including the target at 52, determining access to the vehicle based on the identity and/or status at 54, and controlling a starter of the vehicle at 56.

Non-invasive detection of one or more analytes is performed at 42. The non-invasive detection of the one or more analytes is at a target that is part of an individual seeking access according to method 40. The non-invasive detection at 42 can be performed using a sensor such as the sensor 5 described above and shown in FIG. 1. Detection of the one or more analytes at 42 can include generating a transmit signal 44. The transmit signal can be generated at 44 by a transmit circuit of a sensor, such as transmit circuit 15 of sensor 5 as described above and shown in FIG. 1. The detection of the one or more analytes at 42 can also include transmitting the transmit signal into the target 46. The transmit signal can be transmitted into the target by a transmit antenna of the sensor, such as transmit antenna 11 as described above and shown in FIG. 1. Detection of the one or more analytes at 42 can further include obtaining a response signal 48. The response signal results from the transmitting of the first transmit signal into the target. The first response signal can be obtained using a receive antenna of the sensor such as receive antenna 13 of sensor 5 as described above and shown in FIG. 1. The response obtained at 48 can be processed at 50 to determine a presence or amount of the one or more analytes, for example through converting the received response signal(s) to values indicative of a presence or amount of the one or more analytes.

An identity and/or status of the individual is determined 52 based on the presence or amount of the one or more analytes detected at 42. The identity of the individual can be an identification of the individual including the target as a particular individual, or determining whether the individual including the target is a part of a particular group. The identity can be determined, for example, by comparing the presence or amount of at least some of the one or more analytes to known analyte presences or levels associated with particular individuals or groups that the individual may belong to. The one or more analytes used to determine identity can be, for example, DNA sequences, proteins, hormones, bacteria, viruses, portions thereof, particular conformations thereof, combinations thereof, and/or ratios thereof, and the like. The identity can be a biological identity of the individual based on the one or more analytes. The detected presence or amounts of the one or more analytes can be compared to individual or group profiles including specific analytes, ranges and/or ratios for one or more particular analytes, conditional logic regarding combinations, ratios, or the like of the one or more analytes, or any other suitable information for determining whether an individual meets the profile based on the one or more analytes. The status of the individual can be any transient state that can be characterized by the detection of one or more analytes. Non-limiting examples of statuses of the individual that can be determined based on the one or more analytes at 52 can include a sobriety state, an intoxication state, an alert state, a tired state, certain emotional states such as stress or anger, sympathetic or parasympathetic nervous states, blood sugar levels, and the like. For example, a sobriety state or an intoxication state can be determined based on the presence or absence of recreational drugs, or amounts of such recreational drugs exceeding predetermined thresholds. Other states can be based on other suitable analytes such as prescription or over-the-counter drugs, metabolites, hormones, bacteria, viruses, or particular levels, combinations, or ratios thereof. For example, a communicable disease state can be based on a presence or absence of one or more pathogens of interest among the detected one or more analytes. The status of the individual can be determined by comparing at least some of the one or more analytes detected at 42 to criteria for one or more statuses to be determined. The criteria for the statuses can include the presence and/or amount of one or more analytes, conditional logic regarding combinations or ratios of a plurality of analytes, or any other suitable. In an embodiment, the status criteria can be particular to an individual. In an embodiment, the status criteria can be applied to any individual seeking access according to method 40. At 52, one or both of the identity of the individual and the status of the individual seeking access can be determined based on the one or more analytes detected at 42.

Access to the vehicle is determined at 54, based on one or both of the identity and the status of the individual. In an embodiment, the identity of the individual can be used to determine the access to the vehicle at 54. For example, when the identity of the individual matches an individual permitted access to the vehicle, such as an owner, lessee, or renter of the vehicle, or an employee or other agent of an owner, lessee, or renter, or the like. In an embodiment, the identity of the individual can be compared to a list of individuals or groups to be denied access, and access denied accordingly if the individual is a person or part of a group to be denied access. In an embodiment, the identity can be a confirmation of the individual having characteristics matching a group or class that can have access to the vehicle. In an embodiment, the status of the individual can be used to determine access to the vehicle at 54. The access can be granted or denied based on the presence or absence of one or more statuses or combinations thereof determined at 52. For example, access to the vehicle can be denied when intoxication is determined at 52, and access can be granted when sobriety is determined at 52 or when intoxication is not determined at 52. The access determination at 54 can be based on any status or combinations thereof, such as requiring both sobriety and alertness to be determined in order for access to be provided to vehicle. In an embodiment, both the identity and the status can be used in determining access to the vehicle at 54, for example, requiring both that the identity of the individual match that of a permitted access to the vehicle, while also requiring the presence or absence of one or more certain states in order for the access to be granted, with access denied to other individuals and/or when a person of the proper identity is in a state preventing the granting of access or lacking a state required for granting of access. In an embodiment, one or more additional factors can further be included in the determination of access at 54. For example, the date, time, current or predicted ambient conditions (for example, weather), and the like can further be used in a determination of access. For example, in addition to identity and/or status, access to a device can be conditioned on the access being sought within a permitted time of day, such as during working hours, being during daylight hours, being on particular dates, when a device is within a particular location, and the like. For example, an individual can be granted access during particular ranges of dates, such as periods of rental of the vehicle. In an embodiment, current or predicted ambient conditions such as temperature, precipitation, and the like can be a further condition on which the access is determined, for example, blocking use of a vehicle based on precipitation, visibility, or other such factors affecting use of the vehicle or the safety or risk thereof. The conditioning of use on the vehicle can be based on one or more of these additional factors even when the identity and/or status of the user would otherwise lead to a determination of access to the vehicle. In an embodiment, the access granted can be partial access, such as an ability to start an engine of a vehicle but not to put it into gear to drive, for example to allow a permitted user of the vehicle based on identity to use vehicle electronics or charging capabilities even when their status is not acceptable to actually drive the vehicle.

An access mechanism of the vehicle is operated at 56. The access mechanism operated at 56 can be any suitable mechanism for controlling access to or use of the vehicle. The access mechanism can be a starter for the engine used in the vehicle, for example an ignition for a combustion engine, a controller of an electric or a combustion engine, or any other suitable device capable of controlling starting of the vehicle. Control of the starter is according to the access determination made at 54, for example by starting an engine or preventing starting of the engine based on the determination made at 54. In an embodiment, instead of a starter, a shifter of the vehicle can instead be the access mechanism and controlled according to the access determination made at 54, for example by allowing or preventing the driver from shifting out of a parking state to a driving state such as putting the vehicle into gear. In embodiments, the access mechanism can be locks of the vehicle, which are controlled according to the access determination. In an embodiment, control of the access mechanism 56 can include providing access information to the individual seeking access, such as a passcode to be entered such as an alphanumeric code, an image or code to be scanned such as a QR code, or the like. The individual can then present the access information to an access interface of the vehicle in order to obtain the desired access, for example by inputting the code, scanning the information from a display such as a display of a mobile device, or the like.

Figure 3:
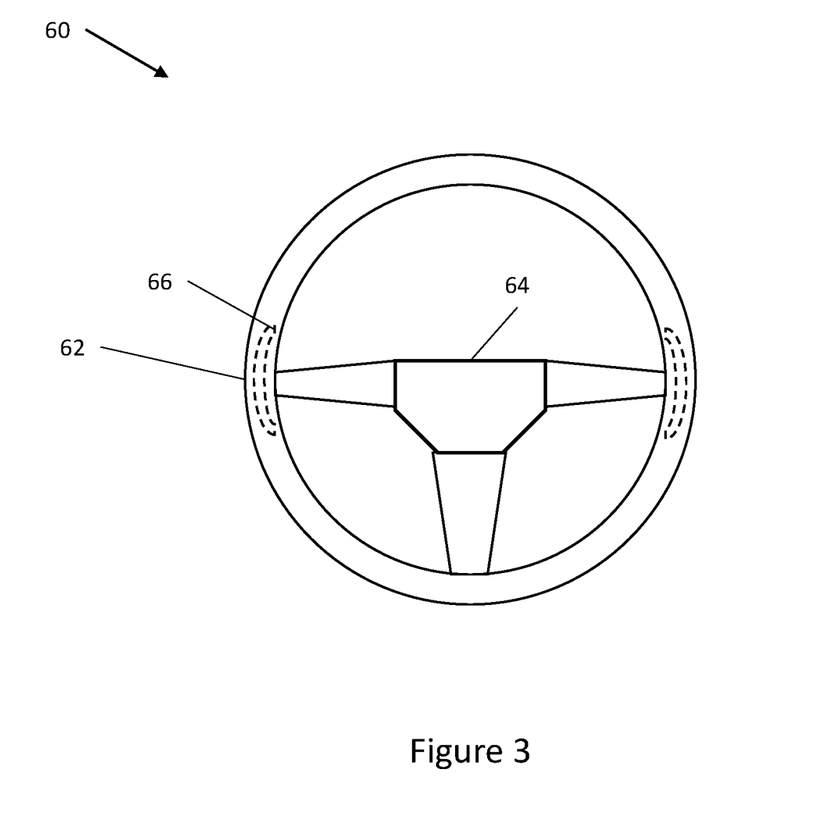
FIG. 3 shows steering wheel of a vehicle according to an embodiment.

FIG. 3 shows steering wheel of a vehicle according to an embodiment. Steering wheel 60 includes a gripping area 62 surrounding a center 64. One or more sensors 66 can be disposed within the gripping area 62. The sensor 66 is a non-invasive sensor capable of detecting one or more analytes in the subject. The sensor 66 can be a sensor such as sensor 5 discussed above and shown in FIG. 1. The sensor 66 can be positioned within gripping area 62 such that a hand of a user is positioned proximate to the sensor in a typical grip on the steering wheel 60 during a starting operation of the vehicle including steering wheel 60. The sensor 66 can detect the presence and/or amount of the one or more analytes in at least one hand of a potential driver gripping the steering wheel. The sensor 66 can communicate with a controller such as a controller 19 or 33 as described above and shown in FIG. 1, either included in the vehicle, a mobile device, or a remote server. The communication can be wired or wireless. In an embodiment, the sensor 66 communicates the response signal to a controller for processing to detect the presence and/or amount of one or more analytes. In an embodiment, the sensor 66 is configured to process the response signal to detect the presence and/or amount of the one or more analytes, and to communicate the presence and/or amount of the one or more analytes to another controller to determine the identity and/or status of the potential driver and in turn determine access to the vehicle.

Figure 4:
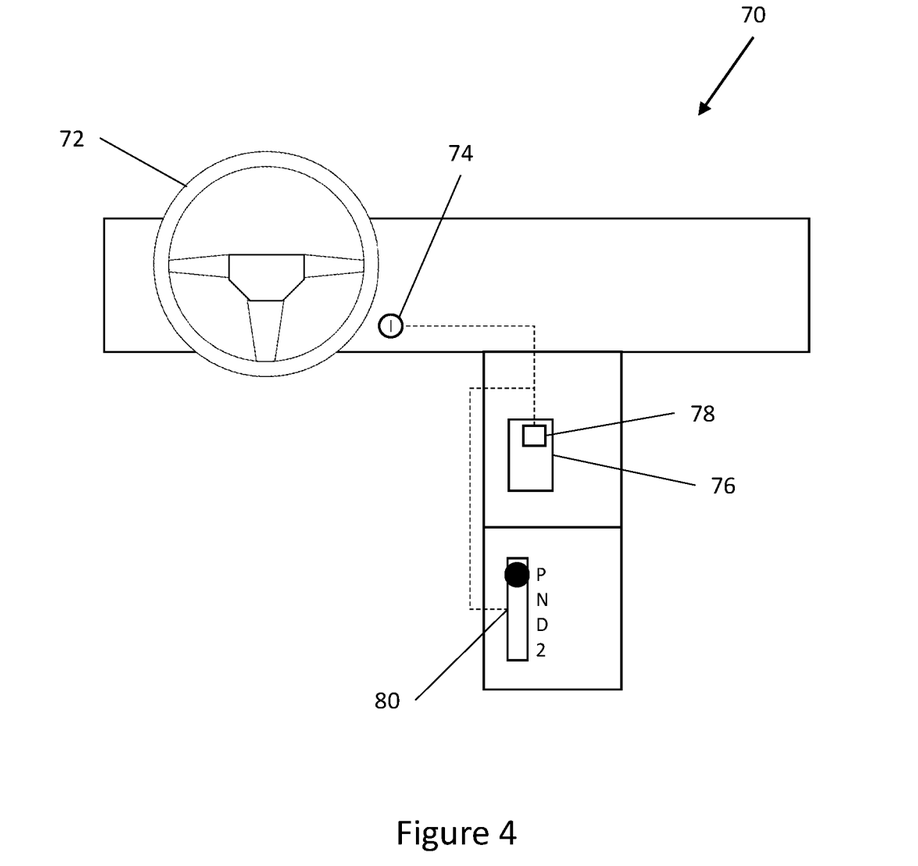
FIG. 4 shows a driver's side of a vehicle according to an embodiment.

FIG. 4 shows a driver's area of a vehicle according to an embodiment. Driver's area 70 includes a steering wheel 72, a starter 74, an access interface 76 including a controller 78, and a shifter 80. Driver's area 70 can be a cockpit of a vehicle, a driver's side of a vehicle, or the like. Driver's area 70 can be, for example, the portion of a car interior within arm's reach of the driver when seated in the driver's seat. Steering wheel 72 can be included in the driver's area 70. The steering wheel 72 can optionally include one or more sensors, such as sensors 66 of the steering wheel 60 shown in FIG. 3 and described above. A starter 74 can be present in the driver's area 70. The starter 74 can be any suitable starter for controlling starting of the vehicle including the driver's area 70. In the embodiment shown in FIG. 4, starter 74 is a keyed ignition for an engine of the vehicle. In an embodiment, the starter 74 can be a push-button starter for an electric or combustion engine, or an interface with a controller configured to start an engine such as an electric or combustion engine. The starter 74 can be controlled to allow or prevent starting of the engine of the vehicle according to access permissions, for example those determined by a controller 78 based on detection of one or more analytes by a sensor, for example a sensor included in the steering wheel 72 or access interface 76. In embodiments, an access interface 76 can be provided in the driver's area 70. The access interface 76 can include a surface or other feature allowing a potential driver to place a part of their body in proximity to a sensor, such as sensor 5 discussed above and shown in FIG. 1, to allow the sensor to detect the one or more analytes in the potential driver. The access interface 76 can alternatively or additionally interface with a device or server such as external device 25 or remote server 27 as shown in FIG. 1 and discussed above, to receive data regarding the presence and/or amount of one or more analytes, identities or statuses determined based on the presence and/or amount of the one or more analytes, and/or access determinations made based on the identity and/or status. Controller 78 can be included in access interface 76 or elsewhere within the vehicle including driver's area 70. Controller 78 can be configured to process responses obtained by the sensor to determine a presence and/or amount of the one or more analytes, and/or make determinations based on the detected presence and/or amount of the one or more analytes such as to determine identities or statuses, or determine access to operate the vehicle. Controller 78 can communicate with starter 74 to permit or deny starting of the vehicle based on the determination of access to the vehicle. Shifter 80 can be a control used by the driver to control operation of the vehicle, for example putting the vehicle into gear to enable forwards or reverse driving of the vehicle. In an embodiment, controller 78 can communicate with shifter 80 to permit or deny operations of the vehicle such as putting the vehicle into gear such that the vehicle can be driven. In an embodiment, the control of the starter 74 and the shifter 80 can be such that a vehicle can be started, for example to access electronics or charging capabilities of the vehicle, but preventing the vehicle from being driven, for example when a driver has a proper identity to use the vehicle but their current state would not allow driving of the vehicle.

Figure 5:
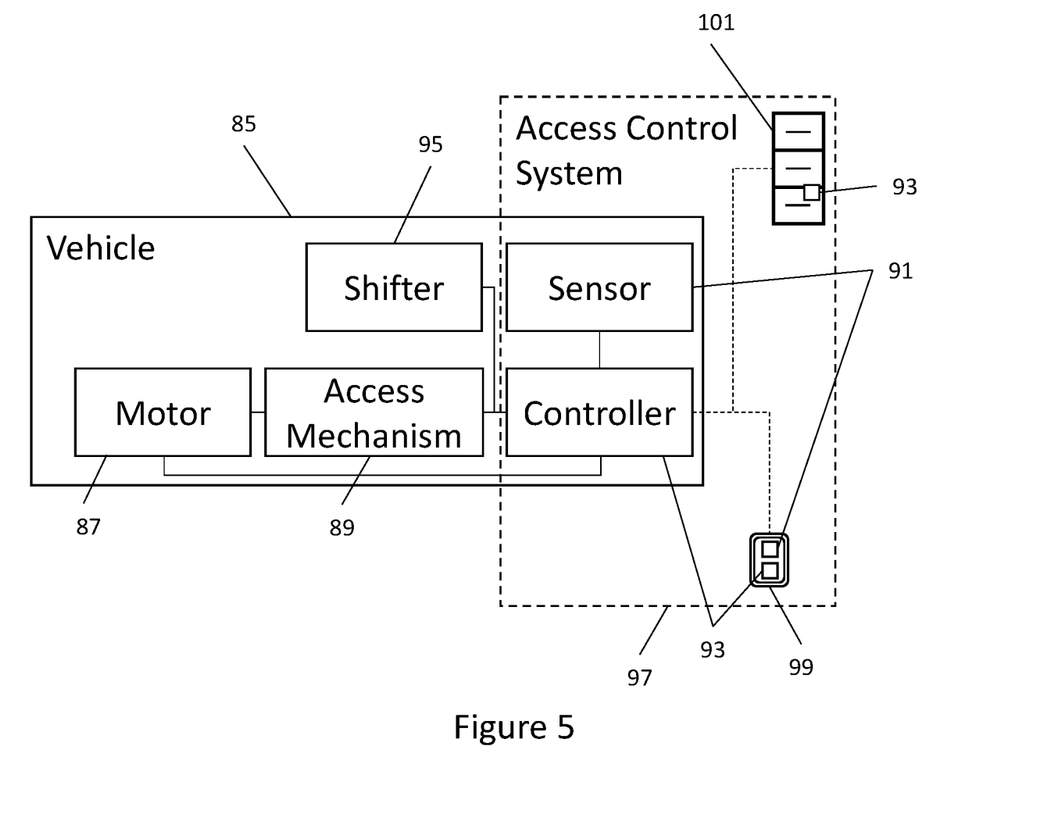
FIG. 5 shows a schematic of a vehicle and an access control system therefor according to an embodiment.

FIG. 5 shows a schematic of a vehicle and an access control system therefor according to an embodiment. Vehicle 85 includes a motor 87, access mechanism 89, a sensor 91, a controller 93, and a shifter 95. The vehicle access control system 97 includes at least sensor 91 and controller 93. The vehicle access control system 97 can optionally further include mobile device 99 and/or remote server 101.

Vehicle 85 is a vehicle for which access is controlled by vehicle access control system. Vehicle 85 can be any suitable vehicle such as an automobile, motorcycle, van, truck, tractors tractor-trailers, construction equipment such as bulldozers or graders and the like, farming equipment such as harvesters, farm tractors, combines and the like, etc. Vehicle 85 can include additional vehicle-specific access controls such as keys, key fobs, and the like. The vehicle 85 is a powered vehicle, having at least one motor 87. Motor 87 is any suitable motor for vehicle 85, such as a combustion motor, for example gasoline or diesel motors, an electric motor, or the like. Vehicle 85 includes access mechanism 89. In an embodiment, the access mechanism 89 is a door lock of the vehicle 85. In an embodiment, the access mechanism 89 is a starter configured to control the starting and/or operation of motor 87. When access mechanism 89 is a starter, the starter can be any suitable starter for the motor 87, such as an ignition, for example a keyed or keyless ignition for a combustion motor, a controller for an electric motor or a combustion motor, or the like. Vehicle 85 can include a shifter 95 configured to allow a driver to control a transmission or other gearing to control a drive mode of the vehicle 85.

Vehicle access control system 97 includes sensor 91 and controller 93. Sensor 91 is a sensor such as sensor 5, configured to non-invasively detect one or more analytes in a potential driver. The detection of the one or more analytes by sensor 91 can be performed when the potential driver is attempting to access the vehicle. Controller 93 is a controller configured to control access mechanism 89 and/or shifter 95 so as to grant or deny access to the vehicle, for example by locking or unlocking one or more doors of the vehicle 85, preventing or allowing starting of the vehicle 85, permitting, denying or limiting the placement of the vehicle 85 into gear by use of the shifter 95, or the like. Controller 93 can further be configured to process a signal obtained by sensor 91 to determine the presence and/or amount of the one or more analytes, determine an identity and/or status based on the one or more analytes, and/or determine an access level based on the identity and/or status. The processing to determine the presence and/or amount of the one or more analytes, determine an identity and/or status based on the one or more analytes, and/or determine an access level based on the identity and/or status can alternatively be performed by other processors, such as additional processors included in vehicle 85, mobile device 99, and/or remote server 101. Controller 93 can control the access mechanism 89 and/or shifter 95 based on the determined access level, whether that value is determined at the controller 93 or if controller 93 receives the access level from another processor.

The sensor 91 and the controller 93 can each be included in the vehicle 85. The sensor 91 can be included, for example, in a steering wheel such as steering wheel 60 described above and shown in FIG. 3, or in an access interface such as access interface 76 described above and shown in FIG. 4. Sensor 91 can instead alternatively be included in mobile device 99, such as a smartphone, wearable device, or the like. Controller 93 can be included in any of vehicle 85 (either in the body of the vehicle or a specific access control device for the vehicle such as a key or key fob), mobile device 99, or remote server 101. The controller 93 can communicate with sensor 91, access mechanism 89, and/or shifter 95 by any suitable wired communications or wireless communications such as Bluetooth, wireless data connections such a 4G, 5G, LTE or the like, or Wi-Fi, as suitable for where sensor 91 and controller 93 are included in vehicle 85, mobile device 99, or remote server 101. In embodiments where additional processors are used to process a signal obtained by sensor 91 to determine the presence and/or amount of the one or more analytes, determine an identity and/or status based on the one or more analytes, and/or determine an access level based on the identity and/or status, these additional processors can be included in any of vehicle 85, mobile device 99, or remote server 101 and be connected accordingly to one another, sensor 91, and/or controller 93. In an embodiment, access information can be provided to the mobile device 99 when it is determined to provide access based on the identity and/or status, which can be input into an access interface so as to gain access to the vehicle.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A vehicle access control system, comprising:
a sensor comprising:
an antenna array having at least one transmit antenna and at least one receive antenna, the at least one transmit antenna is positioned and arranged to transmit a transmit signal into a human target, and the at least one receive antenna is positioned and arranged to detect a response resulting from transmission of the transmit signal by the at least one transmit antenna into the human target;
a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum; and
a receive circuit that is electrically connectable to the at least one receive antenna, the receive circuit is configured to receive a response detected by the at least one receive antenna,
a controller configured to:
determine an identity and/or status of the human target, based on a presence and/or amount of one or more analytes determined by processing of the response; and
determine an access permission for a vehicle based at least in part on the identity and/or status of the individual.

2. The vehicle access control system of claim 1, wherein the sensor is included in the vehicle.

3. The vehicle access control system of claim 1, wherein the sensor is included in a mobile device and the mobile device includes an antenna configured to send a communication signal to the vehicle.

4. The vehicle access control system of claim 3, wherein the controller is included in the mobile device.

5. The vehicle access control system of claim 3, wherein the controller is included in the vehicle.

6. The vehicle access control system of claim 3, wherein the controller is disposed at a remote server.

7. The vehicle access control system of claim 1, wherein the access permission is based on the identity of the human target.

8. The vehicle access control system of claim 1, wherein the access permission is based on the status of the human target.

9. The vehicle access control system of claim 8, wherein the status is based on an amount of the one or more analytes in the human target.

10. The vehicle access control system of claim 9, wherein the one or more analytes include one or more intoxicants.

11. The vehicle access control system of claim 1, wherein the access permission is based on both the identity and the status of the human target.

12. A vehicle, comprising:
an access mechanism;
an access control sensor comprising:
an antenna array having at least one transmit antenna and at least one receive antenna, the at least one transmit antenna is positioned and arranged to transmit a transmit signal into a human target, and the at least one receive antenna is positioned and arranged to detect a response resulting from transmission of the transmit signal by the at least one transmit antenna into the human target;
a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum; and
a receive circuit that is electrically connectable to the at least one receive antenna, the receive circuit is configured to receive a response detected by the at least one receive antenna,
a controller configured to:
determine an identity and/or status of the human target, based on a presence and/or amount of one or more analytes determined by processing of the response; and
control the access mechanism based on the determined identity and/or status of the human target.

13. The vehicle of claim 12, wherein the access control is an ignition of the vehicle.

14. The vehicle of claim 12, wherein the access control is a controller configured to control an electric motor of the vehicle.

15. The vehicle of claim 12, wherein the access control is a door lock of the vehicle.

16. The vehicle of claim 12, wherein the sensor is disposed in a control of the vehicle.

17. The vehicle of claim 16, wherein the control of the vehicle is a steering wheel of the vehicle.

18. The vehicle of claim 12, wherein the sensor is disposed in a panel provided in a driver section of the vehicle.

19. A method of controlling use of a vehicle, comprising:
non-invasively detecting one or more analytes, wherein non-invasively detecting the one or more analytes includes:
generating a transmit signal using a transmit circuit of a sensor;
transmitting the transmit signal into a human target using a transmit antenna of the sensor, the transmit signal in a radio or microwave frequency range of the electromagnetic spectrum;
detecting a response resulting from transmitting the transmit signal into the human target using a receive antenna of the sensor; and
processing the response to determine a presence or amount of the one or more analytes in the human target;
determining, based on the presence or amount of the one or more analytes in the human target, an identity and/or status of the human target; and
operating an access mechanism of the vehicle based on the identity and/or status of the human target.

20. The method of claim 19, wherein operating the access mechanism of the vehicle includes preventing access to or operation of the vehicle when the status of the individual includes intoxication.

21. A method of controlling use of a motor vehicle, comprising:
confirming a biological identity of an individual using a non-invasive sensor by transmitting, using at least one transmit antenna, first transmit signals in a radio or microwave frequency range of the electromagnetic spectrum into the individual and detecting responses resulting from transmitting the first transmit signals into the individual using at least one receive antenna;
determining a presence and/or amount of an analyte in the individual using a non-invasive sensor by transmitting, using at least one transmit antenna, second transmit signals in a radio or microwave frequency range of the electromagnetic spectrum into the individual and detecting responses resulting from transmitting the second transmit signals into the individual using at least one receive antenna;
permitting or blocking access to or operation of the motor vehicle based on the confirming and the determining.

22. The method of claim 21, wherein the non-invasive sensor used in the confirming is the same non-invasive sensor used in the determining.

23. The method of claim 21, wherein the non-invasive sensor used in the confirming is different from the non-invasive sensor used in the determining.

\* \* \* \* \*